United States Patent [19]

Behnke et al.

[11] Patent Number: 5,354,275

[45] Date of Patent: Oct. 11, 1994

[54] INJECTION OR SAMPLING SITE

[75] Inventors: Brett A. Behnke, Hastings; Jon M. Nornberg, Woodbury; Gary A. Thill, White Bear Lake, all of Minn.

[73] Assignee: Minnesota Mining and Manufacturing Company, St. Paul, Minn.

[21] Appl. No.: 121,065

[22] Filed: Sep. 13, 1993

[51] Int. Cl.[5] .............................................. A61M 5/00
[52] U.S. Cl. ..................................... 604/86; 604/256
[58] Field of Search ................ 604/86, 88, 167, 244, 604/256, 411, 415, 905; 128/764, 766; 251/149.1; 215/247

[56] References Cited

U.S. PATENT DOCUMENTS

| | | |
|---|---|---|
| 1,180,665 | 4/1916 | McElroy . |
| 2,546,672 | 3/1951 | Le Clair .............................. 184/105 |
| 3,853,127 | 12/1974 | Spademan ....................... 128/214.4 |
| 3,977,400 | 8/1976 | Moorehead ..................... 128/214.4 |
| 4,219,912 | 9/1980 | Adams ............................... 128/214 |
| 4,243,034 | 1/1981 | Brandt ............................. 128/214.4 |
| 4,634,424 | 1/1987 | O'Boyle ............................... 604/51 |
| 4,723,550 | 2/1988 | Bales et al. ......................... 128/344 |
| 4,752,287 | 6/1988 | Kurtz et al. ......................... 604/99 |
| 4,776,843 | 10/1988 | Martinez et al. .................... 604/86 |
| 4,809,679 | 3/1989 | Shimonaka et al. ................. 128/4 |
| 4,857,062 | 8/1989 | Rusell ................................ 604/256 |
| 4,874,369 | 10/1989 | Kulle et al. .......................... 604/86 |
| 4,889,527 | 12/1989 | Herrli ................................. 604/29 |
| 4,932,409 | 6/1990 | Hirschberg ......................... 128/419 |
| 4,960,412 | 10/1990 | Fink .................................. 604/167 |
| 5,080,654 | 1/1992 | Picha et al. ........................ 604/167 |
| 5,100,394 | 3/1992 | Dudar et al. ....................... 604/283 |
| 5,135,489 | 8/1992 | Jepson et al. ....................... 604/48 |
| 5,158,554 | 10/1992 | Jepson et al. ..................... 604/283 |
| 5,167,648 | 12/1992 | Jepson et al. ..................... 604/283 |
| 5,171,234 | 12/1992 | Jepson et al. ..................... 604/283 |
| 5,188,620 | 2/1993 | Jepson et al. ..................... 604/283 |
| 5,201,725 | 4/1993 | Kling ................................ 604/284 |
| 5,203,775 | 4/1993 | Frank et al. ....................... 604/256 |
| 5,211,634 | 5/1993 | Vaillancourt ...................... 604/167 |
| 5,215,537 | 6/1993 | Lynn et al. ........................ 604/244 |
| 5,242,393 | 9/1993 | Brimhall et al. ..................... 604/86 |
| 5,295,657 | 3/1994 | Atkinson ......................... 251/149.1 |
| 5,295,658 | 3/1994 | Atkinson et al. ................ 251/149.1 |

FOREIGN PATENT DOCUMENTS

| | | |
|---|---|---|
| 8425197.2 | 10/1985 | Fed. Rep. of Germany . |
| 2049513 | 3/1971 | France . |
| 2439022 | 5/1980 | France . |
| WO94/03373 | 2/1994 | PCT Int'l Appl. . |

OTHER PUBLICATIONS

Special Report and Product Review entitled "Needlestick-Prevention Devices"; Health Devices, vol. 20, No. 5, May 1991, pp. 154-180.

*Primary Examiner*—John D. Yasko
*Assistant Examiner*—Anthony Gutowski
*Attorney, Agent, or Firm*—Gary L. Griswold; Walter N. Kirn; Stephen W. Bauer

[57] ABSTRACT

An injection or sampling site adapted to receive a blunt cannula includes a housing having an outside end with a passageway extending inwardly from the outside end, the passageway defining an axial direction; and an elastomeric septum closely received in the passageway of the housing. There is a slit extending through the septum generally in the axial direction which is formed by a hole through the septum that is flattened against itself to seal against itself when the septum is assembled in the housing. Either the septum-receiving portion of the housing or the septum itself has a generally elliptical cross-section to preferentially compress the hole in the septum to form the slit.

24 Claims, 6 Drawing Sheets

INJECTION OR SAMPLING SITE

BACKGROUND AND SUMMARY OF THE INVENTION

This invention relates generally to infusion therapy and IV injection or sampling sites, and more particularly to an injection or sampling site, such as an IV injection site, adapted for use with a blunt cannula.

In an effort to reduce the risk of transmitting infectious diseases, such as hepatitis and AIDS, via accidental needle sticks, various designs of IV injection sites have been developed that are adapted to receive a blunt cannula and/or shielded cannula. See, e.g., Special Report and Product Review, Needlestick-Prevention Devices, Health Devices, pages 154–180 (ECRI, Plymouth Meeting, Pa. 1991). One approach has been to employ a slit septum Y-site in which a slit elastomeric septum is compressed in the Y-site housing. A blunt cannula can be introduced through the slit of the septum, and assuming the design works as intended, the septum will seal against the cannula shaft. When the cannula is removed, the septum seals itself.

Injection sites of this type are either available from or publicized by Baxter International, Inc., Deerfield, Ill., under the trade designation "Baxter's Needle-Less Injection Sites"; Abbott Laboratories, Inc., Abbott Park, Ill., under the trade designation "LifeShield Infection Control System"; and Kendall McGaw Laboratories, Inc., Irvine, Calif., under the trade designation "Safe-Line No-Needle I.V. System". A blunt cannula has been available from Becton, Dickinson and Company, Paramus, N.J., under the trade designation "Interlink System".

In many of these systems the slitting of the septum is critical to their proper functioning. The slit in the septum is created in a secondary operation after the molding of the septum is complete. The slitting of the septum often requires precise accuracy in the location of the slit. Moreover, custom-made tools, secondary operations and subsequent testing are often required to form acceptable leak-resistant slits.

The injection or sampling site of the present invention provides a reliable, leak-resistant site for the introduction of blunt cannula. The injection or sampling site is easier to make and less expensive than previously available injection or sample sites because the slit can be formed in the septum at the time the septum is made, rather than in a separate step after the septum is made. This eliminates the difficulties in accurately cutting the slit in the septum, and the creation of particulate matter resulting from such cutting operations. This further eliminates the need for the special tooling, and the resulting tooling maintenance, to form the slit in the septum in a separate manufacturing step.

The injection or sampling site of the present invention is adapted to receive a blunt cannula. Generally, the injection or sampling site comprises a housing having an outside end and a passageway extending inwardly from the outside end, the passageway defining an axial direction, and an elastomeric septum closely received in the passageway of the housing, the septum having inside and outside ends relative to the outside end of the housing. There is a slit extending through the septum generally in the axial direction. The slit is formed by a hole through the septum that is flattened against itself to seal against itself when the septum is assembled in the housing. The passageway of the housing includes a septum-receiving portion, and one of the septum-receiving portion and the septum has a generally elliptical cross section to preferentially compress the hole in the direction between either the corresponding shorter dimension of the elliptical septum-receiving portion or the corresponding longer dimension of the elliptical septum.

In one embodiment of the injection or sampling site, the septum has a generally elliptical cross-section having longer and shorter dimensions, and the housing is generally cylindrical, so that the hole through the septum is preferentially compressed in the direction along the longer dimension of the septum. The hole in the septum can have a circular cross-section before installation in the housing, but the hole preferably has a generally elliptical cross-section, with the longer dimension of the elliptical bore being aligned with the shorter dimension of the generally elliptical septum and the shorter dimension of the bore being aligned with the longer dimension of the generally elliptical septum.

In another embodiment of the injection or sampling site, the septum has a generally circular cross-section, and the housing has a generally elliptical cross-section having longer and shorter dimensions, so that the hole through the septum is preferentially compressed along the direction of the shorter dimension of the housing.

Thus, the injection or sampling device of the present invention provides a site for the introduction of a blunt cannula. The site is of simple construction, and can be made with a septum having a hole preformed therein, eliminating the need for a separate slit-forming step, and the attendant problems of properly locating the slit, and providing the specialized tooling to properly form the slit. The injection or sampling site is thus faster and easier to manufacture than prior designs, and should result in cost savings and quality improvements.

These and other features and advantages of the invention will be in part apparent and in part pointed out hereinafter.

BRIEF DESCRIPTION OF THE DRAWINGS

Corresponding reference numerals indicate corresponding parts throughout the several views of the drawings.

DETAILED DESCRIPTION OF THE PREFERRED EMBODIMENTS

Figure 1:
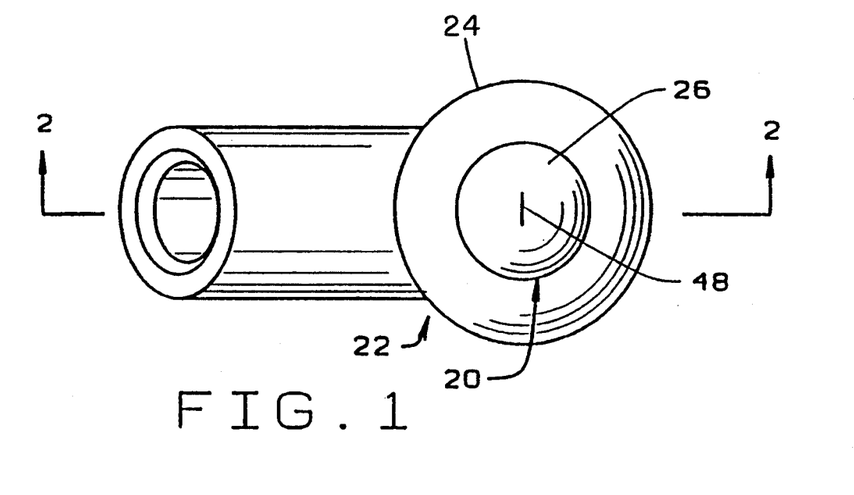
FIG. 1 is a top plan view of a Y-site IV injection site incorporating a first embodiment of an injection site constructed according to the principles of this invention.
Figure 2:
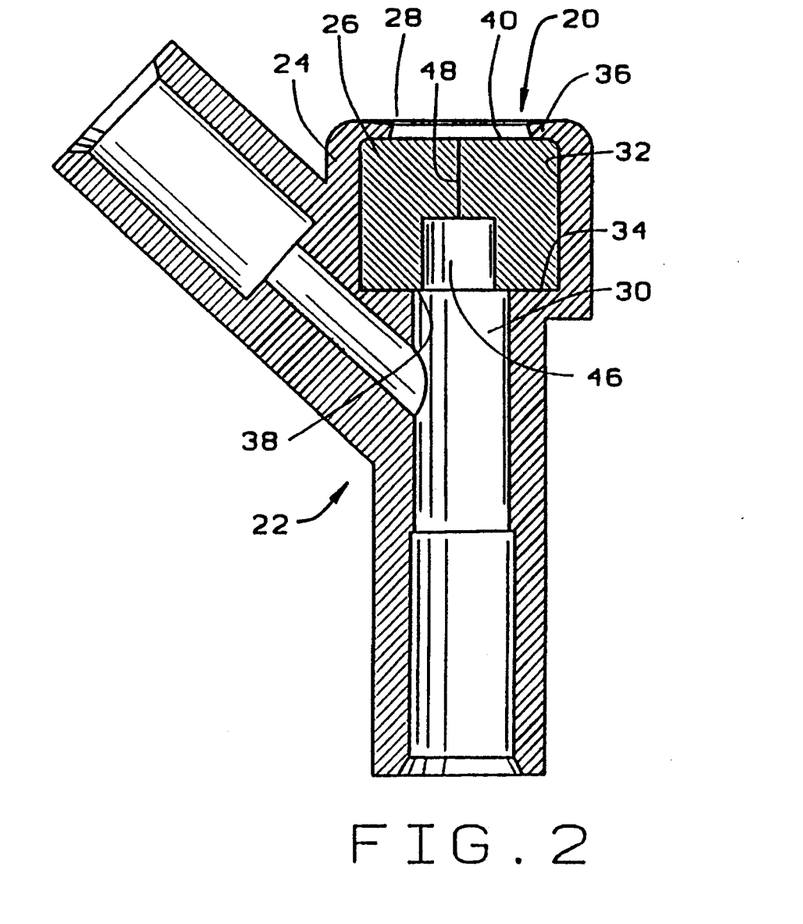
FIG. 2 is a longitudinal cross-sectional view of the Y-site IV injection site, taken along the plane of line 2—2 in FIG. 1.

A first embodiment of an injection or sampling site constructed according to the principles of this invention, indicated generally as 20, is shown in FIGS. 1 and 2 as it would be incorporated into a Y-site IV injection site 22. Although the injection and sampling site of this invention is shown and described as part of a Y-site IV injection site, the invention is not so limited and can be applied to any type of medical injection or sampling sites, for example IV administration tubing sets, or drug vials, etc.

As shown in FIGS. 1 and 2, the injection site 20 comprises a housing 24 and a septum 26. The housing 24 has an outside end 28 and a passageway 30 extending inwardly from the outside end. The passageway 30 defines an axial direction. The passageway 30 includes a septum-receiving portion 32 which in this first embodiment is generally cylindrical, with a generally circular cross section. The inner end of the septum-receiving portion 32 is defined by a shoulder 34 in the passageway 30, and the outer end of the septum-receiving portion is defined by a flange 36 for retaining the septum 26 in the housing 24.

The septum 26 is preferably made from an elastomeric material, such as natural rubber, for example, the natural rubber available under the trade designation "5135 Rubber" from The West Co., Lionville, Pa. The housing 24 is preferably formed of relatively rigid synthetic resin material, including thermoplastic or thermoset materials, such as co-polyester material available under the trade designation "DN003" from Eastman Chemical Co., Kingsport, Tenn.

Figure 3:
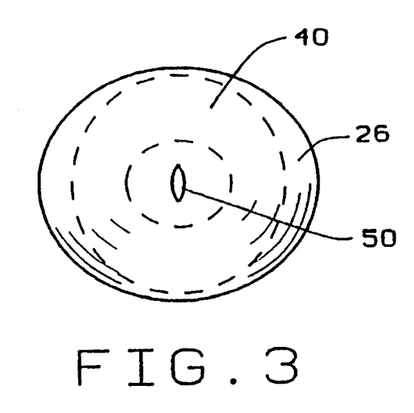
FIG. 3 is a top plan view of the septum before assembly into the injection site of the first embodiment.
Figure 4:
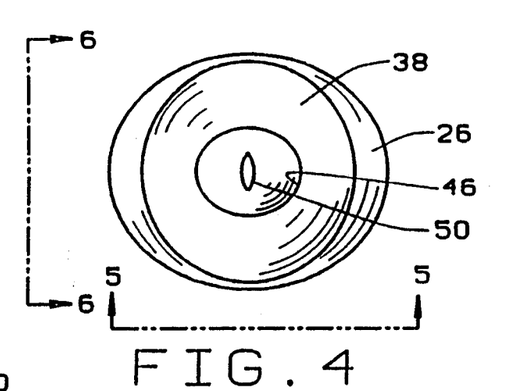
FIG. 4 is a bottom plan view of a septum before assembly into the injection site of the first embodiment.
Figure 5:
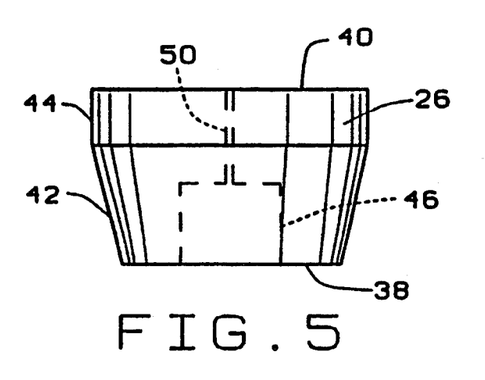
FIG. 5 is a side elevation view of the septum taken along line 5—5 in FIG. 3.
Figure 6:
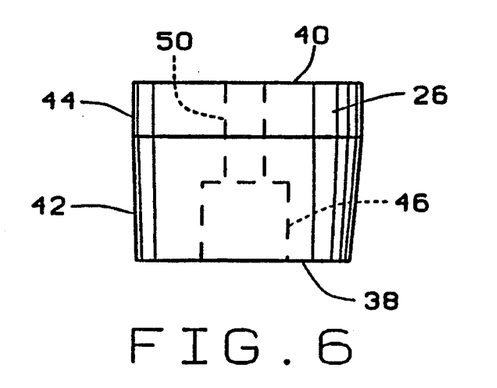
FIG. 6 is a side elevation view of the septum taken along line 6—6 in FIG. 3.

The septum 26 is closely received in the septum-receiving portion 32 of the passageway 30 of the housing 24. The septum 26 has inside and outside ends 38 and 40, respectively. The inside end of the septum 26 is generally circular, as shown in FIG. 4. The outside end 40 of the septum 26 is generally elliptical, as shown in FIG. 3, with a longer dimension and a shorter dimension, corresponding to the major and minor axes of the ellipse. The inside end 38 of the septum 26 abuts the shoulder 34 in the passageway 30. The flange 36 retains the outside end 40 of the septum in the housing 24.

One preferred method and apparatus for swaging the housing to form the flange 36 is described in coassigned U.S. patent application Ser. No. 08/043,466, filed Apr. 2, 1993, by Brett A. Behnke and Gary A. Thill, which is a continuation-in-part of U.S. patent application Ser. No. 07/921,908, filed Jul. 29, 1992, both of which are hereby incorporated herein by reference. See, also, coassigned U.S. patent application Ser. No. 08/072,512, filed Jun. 4, 1993, by Brett A. Behnke and Gary A. Thill, which is also incorporated herein by reference.

Alternatively, the septum 26 could be secured in the housing with an adhesive, and the flange 36 even eliminated. Suitable adhesives may include (a) cyclohexanone available from EM Industries, Inc., Gibbstown, N.J.; (b) cyanoacrylate instant adhesive available under the trade designation "CA-40" from Minnesota Mining and Manufacturing Company, St. Paul, Minn.; or (c) an ultraviolet curable adhesive such as available under the trade designation "LOCTITE 3301 medical grade UV curable adhesive" from Loctite Corp., Newington, Conn. The septum 26 could also be provided with a tubular extension (not shown) on the outside end, that could be folded over the exterior of the housing to secure the septum in the housing, as is know in the art.

In this first preferred embodiment the septum 26 comprises an inner portion 42, adjacent the inside end 38, and an outer portion 44 adjacent the outside end 40. The inner portion 42 tapers from the generally elliptical cross section of the outside end 40 to the generally circular cross-section of the inside end 38. This taper facilitates the insertion of the septum 26 into the passageway 30 of the housing 24. The outer portion 44 has a constant elliptical cross-section. The outer portion 44 helps the septum 26 to seal in the housing 30.

Preferably, a bore 46 extends generally axially into the septum 26 from the inside end 38. The bore 46 preferably extends about 25% to about 50% of the way through the septum 26. As explained below, the bore 46 preferably has a generally elliptical cross-section, with longer and shorter dimensions corresponding to the major and minor axes of the ellipse. The bore 46 is preferably oriented concentrically with the elliptical end of the septum 26, so that their respective longer and shorter dimensions correspond. The bore 46 is preferably shaped so that when the septum 26 is installed in the generally circular passageway 30 of the housing 24, the septum 26 compresses in such a way that the bore 46 assumes a generally circular cross-section.

A slit 48 extends generally axially through the septum 26 from the outside end 40 to the bore 46. The arrangement is such that when a cannula C is introduced through the slit 48 of the septum 26, the elastomeric material of the septum 26 expands into the bore 46 of the septum to sealingly engage the cannula C along the bore of the septum. See FIGS. 14–15. While the bore 46 is preferred, it will be understand that the septum 26 could be provided with the slit 48 but not the bore.

The slit 48 is formed by a hole 50 that extends through the septum 26 from the outside end 40 to the bore 46, when the septum 26 is in its uncompressed state before installation in the housing 24 (see FIGS. 3–6). The hole 50 flattens against itself to seal against itself when the septum 26 is assembled in the housing 24. The hole 50 preferably has a generally elliptical cross-section, with longer and shorter dimensions corresponding to the major and minor axes of the ellipse. The hole 50 is preferably oriented with respect to the septum 26 so that the longer dimension of the hole cross-section is aligned with the shorter dimension of the elliptical outside end 40 of the septum, and the shorter dimension of the hole cross-section is aligned with the longer dimension of the elliptical outside end 40 of the septum.

The hole 50 is preferably not a true ellipse, rather the ends of the hole are preferably sharp so that the hole 50 is better adapted to close on itself and form the slit 48. The hole 50 preferably has a cross-sectional shape corresponding to the intersection of two large diameter circles. As used herein, "large diameter circles" means circles having a large diameter relative to the size of the hole 50 as illustrated in FIGS. 3 and 4.

The septum 26 can be conveniently molded, for example by injection molding, with the hole 50 therein. The septum 26 is then installed in the housing 24. The generally circular inner end 38, and the tapering configuration of the inner portion 42 facilitate the insertion of the septum 26 into the housing 24. The insertion of the septum 26 into the housing 24 causes the septum to compress, this compression causing the generally elliptical bore 46 to assume a generally circular configuration. This compression also causes the generally elliptical hole 50 to close on itself and form the slit 48. The elliptical configuration of the outside end of the septum 26 provides preferential compression to hold the slit 48 closed.

Figure 14:
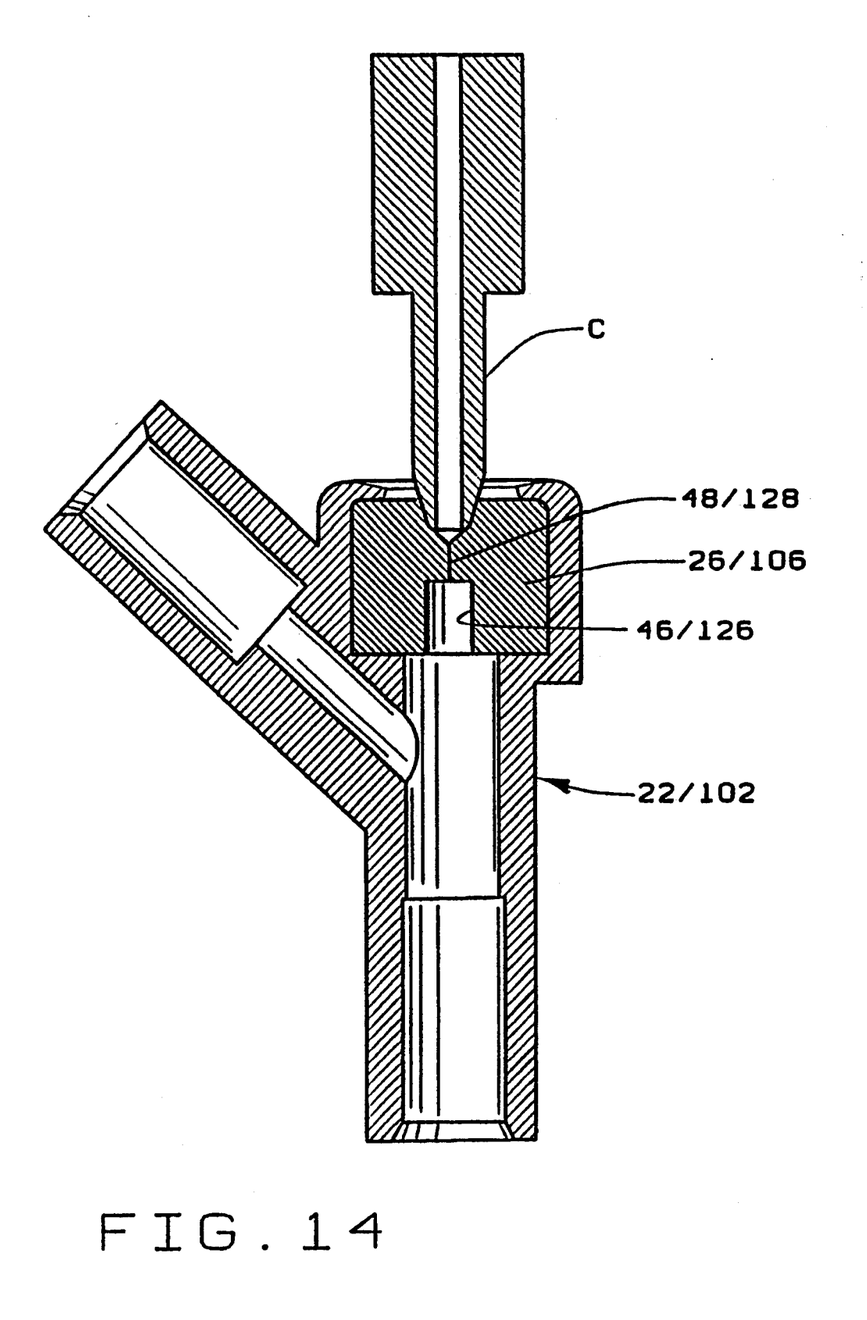
FIG. 14 is a longitudinal cross-sectional view of a Y-site IV injection site incorporating an injection site constructed according to the principles of this invention, showing a blunt cannula partially inserted into the injection site.
Figure 15:
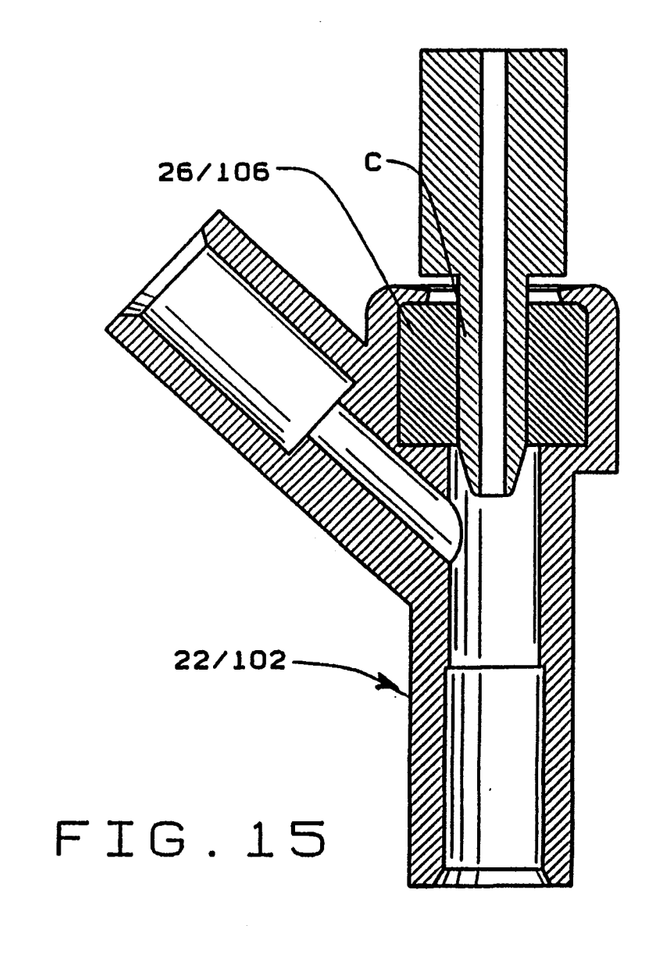
FIG. 15 is a longitudinal cross-sectional view of a Y-site IV injection site incorporating an injection site constructed according to the principles of this invention, showing a blunt cannula fully inserted into the injection site.

As shown in FIGS. 14 and 15, a blunt cannula C can still be introduced into the slit 48, and through the septum 26. As the cannula C progresses through the septum, the septum material displaced by the cannula causes the bore 46 to gradually contract (compare FIG. 14 with FIG. 2), until the bore 46 closely surrounds and seals with the cannula C (see FIG. 15).

Figure 7:
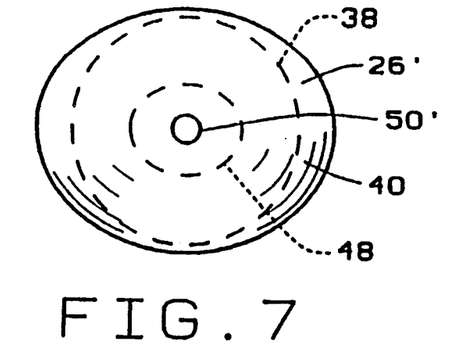
FIG. 7 is a top plan view of an alternate construction of the septum before assembly into the injection site of the first embodiment.
Figure 8:
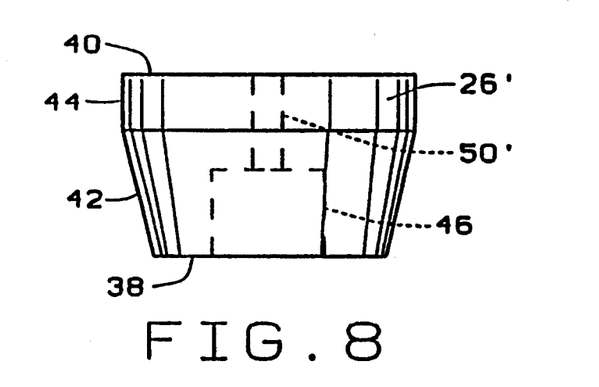
FIG. 8 is a side elevation view of the alternate construction of the septum, taken along line 8—8 in FIG. 7.

An alternate construction of the septum is indicated generally as 26' in FIGS. 7 and 8. The septum 26' is similar to septum 26, and corresponding parts are identified with corresponding reference numerals. However, rather than the generally elliptical hole 50 of the septum 26, the septum 26' has a generally circular hole 50'.

Figure 9:
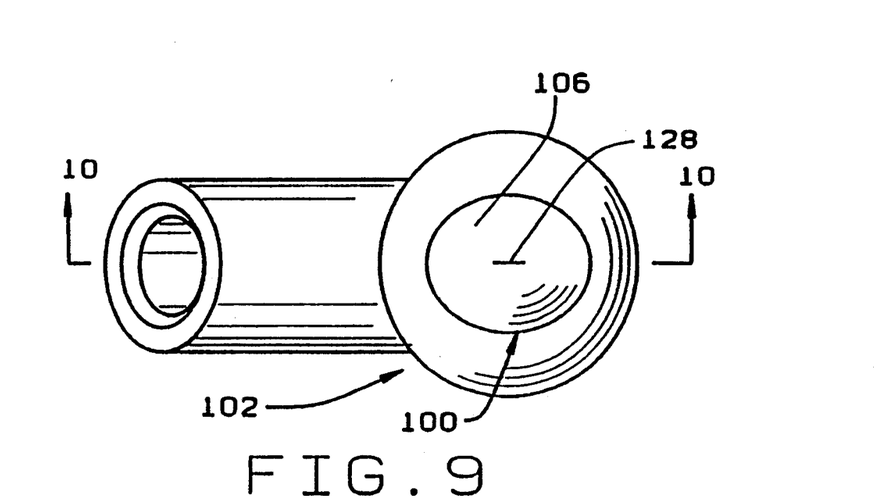
FIG. 9 a top plan view of a Y-site IV injection site incorporating a second embodiment of an injection site constructed according to the principles of this invention.
Figure 10:
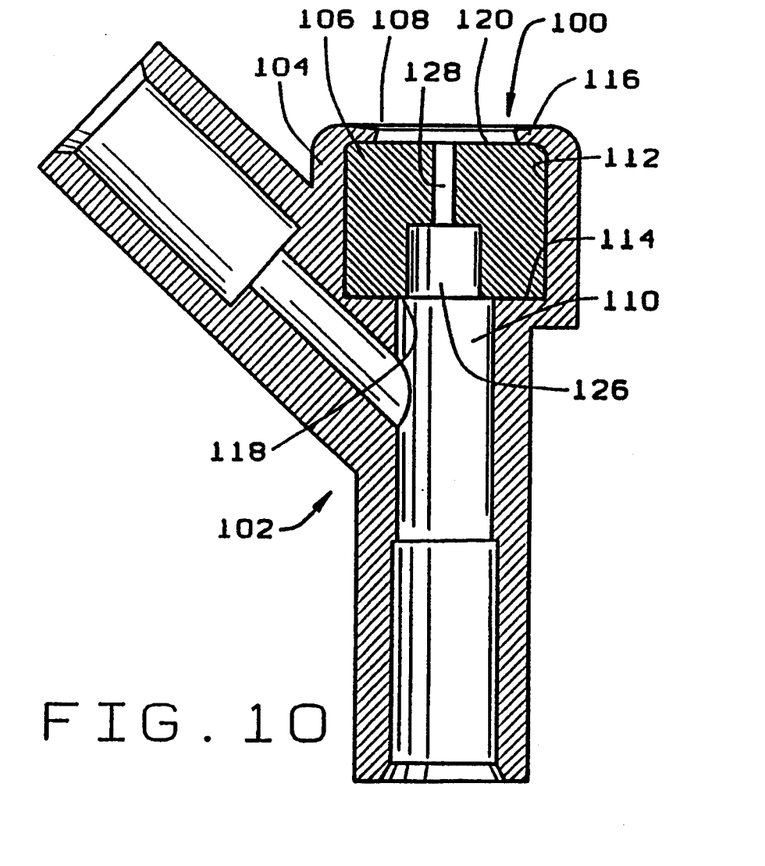
FIG. 10 is a longitudinal cross-sectional view of the Y-site IV injection site, taken along the plane of line 10—10 in FIG. 9.

A second embodiment of an injection or sampling site constructed according to the principles of this invention, indicated generally as 100, is shown in FIGS. 9 and 10 as it would be incorporated into a Y-site IV injection site 102. As explained above, however, this invention is not limited to Y-site IV injection sites.

As shown in FIGS. 9 and 10, the injection site 100 comprises a housing 104 and a septum 106. The housing 104 has an outside end 108 and a passageway 110 extending inwardly from the outside end. The passageway 110 defines an axial direction. The passageway 110 includes a septum-receiving portion 112 which in this second embodiment has a generally elliptical cross section. The inner end of the septum-receiving portion 112 is defined by a shoulder 114 in the passageway 110, and the outer end of the septum-receiving portion is defined by a flange 116 for retaining the septum 106 in the housing 104.

Figure 11:
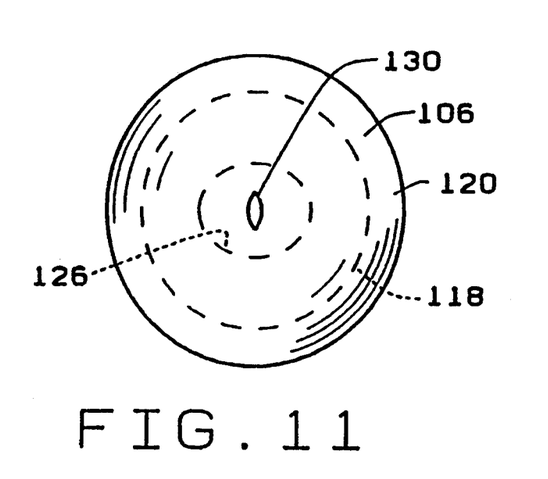
FIG. 11 is a top plan view of the septum before assembly into the injection and sampling site of the second embodiment of the present invention.
Figure 12:
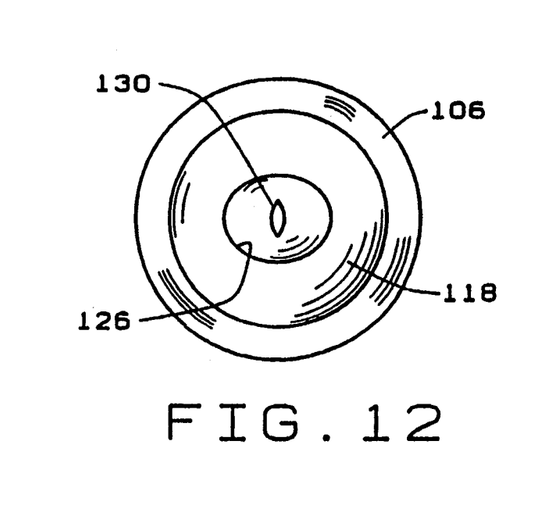
FIG. 12 is a bottom plan view of the septum before assembly into the injection site of the second embodiment.

The septum 106 is preferably made from an elastomeric material. The septum 106 is closely received in the septum-receiving portion 112 of the passageway 110 of the housing 104. The septum 106 has inside and outside ends 118 and 120, respectively. The inside end 118 of the septum 106 is generally circular, as shown in FIG. 12. The outside end 120 of the septum 106 is also generally circular, as shown in FIG. 11, but larger than the inside end 118. The inside end 118 of the septum 106 abuts the shoulder 114 in the passageway 110. The flange 116 retains the outside end 120 of the septum 106 in the housing 104. Some other means for securing the septum 106 in the housing 104 could be used, as described above with respect to septum 26 and housing 24.

In this second embodiment the septum 106 comprises an inner portion 122, adjacent the inside end 118, and an outer portion 124 adjacent the outside end 120. The inner portion 122 tapers from the larger circular cross-section of the outside end 120 to the smaller circular cross-section of the inside end 118. This taper facilitates the insertion of the septum 106 into the passageway 110 of the housing 104. The outer portion 124 has a constant circular cross-section. The outer portion 124 helps the septum 106 to seal in the housing 104.

A bore 126 extends generally axially into the septum 106 from the inside end 118. The bore 126 preferably extends about 25% to about 50% of the way through the septum 106. As explained below the bore 126 preferably has a generally elliptical cross-section, with longer and shorter dimensions corresponding to the major and minor axes of the ellipse. When the septum 106 is installed in the generally elliptical housing, the bore 126 is preferably oriented so that the bore compresses to a generally circular cross-section.

A slit 128 extends generally axially through the septum 106 from the outside end 120 to the bore 126. The arrangement is such that, when a cannula C is introduced through the slit 128 of the septum 106, the elastomeric material of the septum 106 expands into the bore 126 of the septum to sealingly engage the cannula C along the bore of the septum. See FIGS. 14–15.

Figure 13:
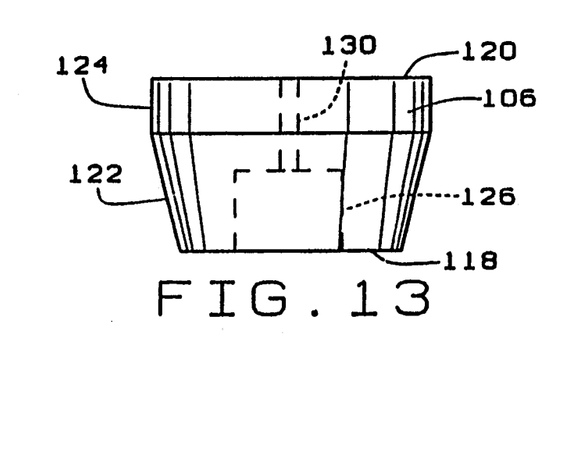
FIG. 13 is a side elevation view of the septum before assembly into the injection and sampling site of the second embodiment.

The slit 128 is formed by a hole 130 that extends through the septum 106 from the outside end 120 to the bore 126, when the septum is in its uncompressed state before installation in the housing 104 (see FIGS. 11–13). The hole 130 flattens against itself to seal against itself when the septum 106 is assembled in the housing 104. The hole 130 preferably has a generally elliptical cross-section, with longer and shorter dimensions corresponding to the major and minor axes of the ellipse. The septum must be oriented with respect to the housing 104 so that shorter dimension of the elliptical hole and the shorter dimension of the elliptical housing coincide, to provide maximum compression to compress the hole 130 into the slit 128. The hole 130 would preferably not be a true ellipse, rather the ends of the hole would preferably be sharp so that the hole is better adapted to close on itself and form the slit 128. The hole 130 preferably has a cross-section corresponding to the intersection of two large diameter circles. Alternatively, the hole 130 could have a generally circular cross-section, so that the alignment of the septum with the generally elliptical housing is not critical.

The septum 106, like septum 26, can be conveniently molded, for example by injection molding, with the hole 130 therein. The septum is then installed in the housing. The tapering configuration of the inner portion 122 facilitates the insertion of the septum into the housing. The insertion of the septum into the housing causes the septum to compress, this compression causing the generally elliptical bore 126 to assume a generally circular configuration. This compression also causes the hole 130 to close on itself and form the slit 128. The elliptical configuration of the housing provides preferential compression to hold the slit 128 closed.

As shown in FIGS. 14 and 15, a blunt cannula C can still be introduced into the slit 128, and through the septum. As the cannula C progresses through the septum, the septum material displaced by the cannula causes the bore 126 to gradually contract (compare FIG. 14 with FIG. 10), until the bore 126 closely surrounds and seals with the cannula (see FIG. 15).

The injection and sampling site 20 of the first embodiment and the injection and sampling site 100 of the second embodiment can be quickly, easily, and inexpensively manufactured. The septum 26 is preferably molded with the hole 50 therein, eliminating the need for a separate slit forming step, avoiding the attendant problems of properly locating the slit, and eliminating the need for special slit forming tooling. However, the bore could be formed after the septum is molded. The formation of a hole is considerably easier than the formation of a slit, and does not require the same special tooling. The injection and sampling site 20 is assembled by installing the septum 26 or 26' with the hole 50 or 50' into the septum-receiving portion 32 of the housing 24. The housing 24 compresses the septum, causing the hole to close upon itself and form the slit 48. The elliptical configuration of the septum provides a preferential compression on the slit.

Similarly, the septum 106 is preferably molded with the hole 130 therein, eliminating the need for a separate slit forming step, avoiding the attendant problems of properly locating the slit, and eliminating the need for special slit forming tooling. However, the hole could be formed after the septum is molded. The formation of a hole is considerably easier than the formation of a slit, and does not require the same special tooling. The injection and sampling site 100 is assembled by installing the septum 106 with the hole 130 into the septum-receiving portion 112 of the housing 104. The housing 104 compresses the septum, causing the hole to close upon itself and form the slit 128. The elliptical configuration of the septum-receiving portion 112 of the housing provides a preferential compression on the slit.

As various changes could be made in the above constructions and methods without departing from the scope of the invention, it is intended that all matter contained in the above description or shown in the accompanying drawing be interpreted as illustrative and not in a limiting sense.

We claim:

1. An injection or sampling site adapted to receive a blunt cannula, the injection or sampling site comprising:
   a housing having an outside end and a passageway extending inwardly from the outside end, the passageway defining an axial direction and having a septum-receiving portion; and
   an elastomeric septum closely received in the passageway of the housing, the septum having inside and outside ends relative to the outside end of the housing, a slit extending through the septum generally in the axial direction, the slit being formed by a hole through the septum that is flattened against itself to seal against itself when the septum is assembled in the housing, wherein, before assembly of the septum into the septum-receiving portion of the housing, the hole in the septum has a generally elliptical cross-section, having a longer dimension and a shorter dimension;
   one of the septum-receiving portion and the septum having a relatively elliptical cross-section and the other of the septum-receiving portion and the septum having a relatively circular cross section to preferentially compress the hole in the direction between either the corresponding shorter dimension of the elliptical septum-receiving portion or the corresponding longer dimension of the elliptical septum.

2. The injection or sampling site according to claim 1 wherein, before assembly of the septum into the septum-receiving portion of the housing, the septum comprises a generally tapering inner portion adjacent the inside end, which tapers toward the inside end.

3. The injection or sampling site according to claim 2 wherein before assembly of the septum into the septum-receiving portion of the housing, the septum has an outer portion, adjacent the outside end of the septum, having a generally uniform cross-section.

4. The injection or sampling site according to claim 1 wherein septum-receiving portion of the housing has a generally elliptical cross-section.

5. The injection or sampling site according to claim 4 wherein, before assembly of the septum into the septum-receiving portion of the housing, the septum has a generally circular cross-section.

6. The injection or sampling site according to claim 4 wherein, before assembly of the septum into the septum-receiving portion of the housing, the septum has a generally tapered inner portion, adjacent the inside end, tapering toward the inner end.

7. The injection or sampling site according to claim 1 wherein, before assembly of the septum into the septum-receiving portion of the housing, the hole in the septum has a cross-section corresponding to the shape of intersection of two large diameter circles.

8. The injection or sampling site according to claim 1 wherein the outside end of the housing is swaged to constrain the elastomeric septum in the passageway of the housing.

9. An injection or sampling site adapted to receive a blunt cannula, the injection or sampling site comprising:
   a housing having an outside end and a passageway extending inwardly from the outside end, the passageway defining an axial direction; and
   an elastomeric septum closely received in the passageway of the housing, the septum having inside and outside ends relative to the outside end of the housing, a slit extending through the septum generally in the axial direction, the slit being formed by a hole through the septum that is flattened against itself to seal against itself when the septum is assembled in the housing;
   the passageway of the housing including a septum-receiving portion, one of the septum-receiving portion and the septum having a relatively elliptical cross-section and the other of the septum-receiving portion and the septum having a relatively circular cross section to preferentially compress the hole in the direction between either the corresponding shorter dimension of the elliptical septum-receiving portion or the corresponding longer dimension of the elliptical septum; and
   wherein:
   (a) before assembly into the septum-receiving portion of the housing, the septum has a generally elliptical cross-section having longer and shorter dimensions, the hole of the septum being preferentially compressed in the direction along the longer dimension of the septum cross-section when inserted into the septum-receiving portion of the housing; and (b) before assembly of the septum into the septum-receiving portion of the housing, the hole in the septum has a generally elliptical cross-section, having a longer dimension and a shorter dimension.

10. The injection or sampling site according to claim 9 wherein the longer dimension of the generally elliptical hole is aligned with the shorter dimension of the generally elliptical cross-section of the septum, and the shorter dimension of the generally elliptical hole being aligned with the longer dimension of the generally elliptical cross-section of the septum so that the housing compresses the septum forming the hole into a slit.

11. The injection and sampling site according to claim 9 wherein, before assembly of the septum into the septum-receiving portion of the housing, the hole in the septum has a cross-section corresponding to the shape of intersection of two large diameter circles.

12. The injection or sampling site according to claim 1 wherein the septum-receiving portion of the housing is generally cylindrical.

13. The injection or sampling site according to claim 1 wherein, before assembly of the septum into the septum-receiving portion of the housing, the septum comprises a generally tapering inner portion, adjacent the inside end, and an outer portion adjacent the outside end having a relatively constant cross-section.

14. The injection or sampling site according to claim 9 wherein the septum-receiving portion of the housing is generally cylindrical.

15. The injection or sampling site according to claim 9 wherein, before assembly of the septum into the septum-receiving portion of the housing, the septum comprises a generally tapering inner portion, adjacent the inside end, and an outer portion, adjacent the outside end having a relatively constant elliptical cross-section.

16. The injection or sampling site according to claim 9 wherein, before assembly of the septum into the septum-receiving portion of the housing, the septum comprises a generally tapering inner portion adjacent the inside end, which tapers toward the inside end.

17. The injection or sampling site according to claim 9 wherein before assembly of the septum into the septum-receiving portion of the housing, the septum has an outer portion, adjacent the outside end of the septum, having a generally uniform elliptical cross-section.

18. The injection or sampling site according to claim 9 wherein the outside end of the housing is swaged to constrain the elastomeric septum within the septum-receiving portion of the passageway of the housing.

19. A method of assembling an injection or sampling site comprising the steps of:
providing a housing having an outside end and a passageway extending inwardly from the outside end, the passageway defining an axial direction and having a septum-receiving portion therein;
providing an elastomeric septum having inside and outside ends relative to the outside end of the housing, with a hole extending through the septum generally in the axial direction;
one of the septum-receiving portion and the septum having a relatively elliptical cross-section and the other of septum-receiving portion and the septum having a relatively circular cross section; and
inserting the septum into the housing to compress the septum and form a slit therein including the step of preferentially compressing the hole in the septum in the direction between either the corresponding shorter dimension of the elliptical septum-receiving portion or the corresponding longer dimension of the elliptical septum to flatten of the hole against itself to seal against itself when the septum is assembled in the housing; wherein, before inserting the septum into the housing, the hole in the septum has a generally elliptical cross-section; the step of inserting the septum into the housing to compress the septum to form a slit therein by the flattening of the hole against itself to seal against itself when the septum is assembled in the housing including:
flattening the generally elliptical cross section of the hole against itself to form a slit extending in the direction of elongation of the generally elliptical hole.

20. The method according to claim 19 wherein the step of providing the septum comprising molding the septum with the hole therein.

21. The method according to claim 19 wherein the step of providing an elastomeric septum comprises making a hole through the septum after the septum is formed.

22. The method according to claim 19 wherein the septum has a generally elliptical cross section before assembly of the septum into the housing and the septum-receiving portion of the passageway of the housing has a generally circular cross section, the step of inserting the septum into the housing to compress the septum and form a slit therein further including:
compressing the generally elliptical cross section of the septum within the septum-receiving portion of the passageway of the housing to deform the septum into a generally circular cross section.

23. The method according to claim 22 wherein the generally elliptical cross sections of the septum and the hole each define a relatively longer dimension and a relatively shorter dimension, the relatively longer dimension of the hole being generally perpendicular to the relatively longer dimension of the septum; the step of flattening the generally elliptical cross section of the hole against itself to form a slit extending in the direction of elongation of the generally elliptical hole including:
flattening the hole against itself to form a slit extending in a direction generally perpendicular to the direction corresponding to the relatively longer dimension of the septum.

24. The method according to claim 19 further comprising the step of swaging the outside end of the housing toward the elastomeric septum to constrain the septum within the septum-receiving portion of the passageway of the housing.

* * * * *